US007789840B2

(12) United States Patent
Nole

(10) Patent No.: US 7,789,840 B2
(45) Date of Patent: Sep. 7, 2010

(54) SYSTEM AND METHOD FOR FOOT CLASSIFICATION

(76) Inventor: Roberta Nole, 67 Fall Mountain Lake Rd., Terryville, CT (US) 06768

( * ) Notice: Subject to any disclaimer, the term of this patent is extended or adjusted under 35 U.S.C. 154(b) by 105 days.

(21) Appl. No.: 11/377,053

(22) Filed: Mar. 15, 2006

(65) Prior Publication Data

US 2006/0213090 A1 Sep. 28, 2006

Related U.S. Application Data

(60) Provisional application No. 60/665,429, filed on Mar. 24, 2005.

(51) Int. Cl.
*A61B 5/103* (2006.01)
*A61F 5/14* (2006.01)
(52) U.S. Cl. .......................... 600/595; 36/140
(58) Field of Classification Search .................. 36/140, 36/129, 88, 91; 600/595, 592, 587
See application file for complete search history.

(56) References Cited

U.S. PATENT DOCUMENTS

| 4,520,581 | A | * | 6/1985 | Irwin et al. ..................... 36/88 |
| 5,659,395 | A | | 8/1997 | Brown et al. |
| 5,790,256 | A | | 8/1998 | Brown et al. |
| 6,331,893 | B1 | | 12/2001 | Brown et al. |
| 6,692,454 | B1 | * | 2/2004 | Townsend et al. ............. 602/27 |
| 6,823,550 | B2 | * | 11/2004 | Kantro ..................... 12/142 N |
| 7,113,162 | B1 | * | 9/2006 | Beasley ...................... 345/102 |
| 2002/0071597 | A1 | | 6/2002 | Ravitz et al. |
| 2007/0043582 | A1 | * | 2/2007 | Peveto et al. ................... 705/1 |

OTHER PUBLICATIONS

Razeghi et al., Foot Type Classification: A Critical Review of Current Methods, (2002) Elsevier, Gait and Posture vol. 15 (2002), pp. 282-291.*
Woodburn et al. Relation between heel postition and the distribution of forefoot plantar pressures and skin callosities in rheumatoid arthritis. Nov. 1996. Annals of the Rheumatic Diseases, v.55(11); 806-810.*
Internet website entitled "*Podiatrychannel*," www.podiatrychannel.com/orthotics, last modified Feb. 8, 2005, printed Mar. 13, 2006.

* cited by examiner

*Primary Examiner*—Max Hindenburg
*Assistant Examiner*—Fangemonique Smith
(74) *Attorney, Agent, or Firm*—Michaud-Kinney Group LLP

(57) ABSTRACT

A method of classifying a foot into a specific foot type selected from a group of twenty-four foot types. The method includes visualizing the foot, in a standing position, or in a walking or running motion, and assessing a plurality of characteristics of the foot. Classification of the foot is based on the aforementioned visualization of the foot and the assessment of the characteristics exhibited by the foot.

18 Claims, 4 Drawing Sheets

| #1 | #2 | #3 | #4 |
|---|---|---|---|
| RF: ≥ (-)7° EV | RF: (-)4-6° EV | RF: (-)1-3° EV | RF: 0° OR +EV |
| FF: ≥7° RIGID VALGUS (CAVUS TORQUE FOOT) | FF: ≥7° RIGID VALGUS | FF: ≥7° RIGID VALGUS | FF: ≥7° VALGUS (RIGID) *PRIMARY FF VALGUS* |
| COMPENSATION: RF / FF DEFORMITIES MAY OFFSET, OR OFTEN THE RF DEFORMITY IS GREATER. LATERAL INSTABILITY IN PROPULSION IS COMMON. | COMPENSATION: THE FF VALGUS IS > THAN THE RF VARUS DEFORMITY, CAUSING MILD STJ SUPINATION IN MIDSTANCE. | COMPENSATION: THE FF VALGUS SUPERCEEDS THE RF DEFORMITY, AND STJ RESUPINATON OCCURS FROM FOOTFLAT THROUGH MIDSTANCE. | COMPENSATION: SINCE THE FF VALGUS IS LARGER AND MORE RIGID THAN THE #8, THERE IS BETTER STJ RESUPINATON IN MIDSTANCE BUT STILL NOT ENOUGH TO OVERCOME THE GROSS RF INSTABILITY. |
| #5 | #6 | #7 | #8 |
| RF: ≥ (-)7° EV | RF: (-)4-6° EV | RF: (-)1-3° EV | RF: 0° OR +EV |
| FF: FLEXIBLE 1-6° VALGUS | FF: FLEXIBLE 1-6° VALGUS | FF: FLEXIBLE 1-6° VALGUS | FF: FLEXIBLE 1-6° VALGUS |
| COMPENSATION: ↓'d LIMB ER VS #9 SINCE THE FF VALGUS PARTIALLY OFFSETS THE RF DEFORMITY. CAVOVALGUS FOOT TYPE. | COMPENSATION: FF VALGUS MAY FUNCTIONALLY OFFSET THE MILD MTJ PRONATION SEEN IN #10, BUT MAY OVERLOAD THE 1ST MTH CAUSING SESAMOID PAIN. | COMPENSATION: THE COMPENSATIONS SEEN IN #11 ARE PARTIALLY REDUCED BY THE FF VALGUS INFLUENCE, FURTHER IMPROVING 1ST RAY FUNCTIONING. | COMPENSATION: THE GROSS INSTABILITY NOTED WITH #12 IS SLIGHTLY REDUCED BY THE FF VALGUS INFLUENCE, LESSENING MIDFOOT SAG. |
| #9 | #10 | #11 | #12 |
| RF: ≥ (-)7° EV | RF: (-)4-6° EV | RF: (-)1-3° EV | RF: 0° OR +EV |
| FF: NORMAL | FF: NORMAL | FF: NORMAL | FF: "NORMAL" |
| COMPENSATION: EXCESSIVE LIMB EXT ROT DURING GAIT. EXCESSIVE LOADING OF LATERAL FOOT. NO MIDFOOT SAG. FALSE + TOE SIGN. | COMPENSATION: PROPOSED IDEAL FOOT TYPE IN THIS FOOT CLASSIFICATION SYSTEM. FOOT WELL BALANCED AT ALL PHASES OF GAIT. MUSCLE FUNCTION / EFFICIENCY OPTIMIZED. | COMPENSATION: SIMILAR TO #12, BUT THE LEVEL OF RESTRICTED STJ EVERSION PARTIALLY LOCKS THE MTJ AND ↓'es MIDFOOT SAG. PERONEAL FUNCTIONING IMPROVED, 1ST RAY PLANTARFLEXES. | COMPENSATION: GROSS INSTABILITY OF TCJ, STJ & MTJ'S, LARGE MEDIAL TALAR SHIFTING, TIBIA INT ROT, LARGE MIDFOOT SAG. MILD TOE SIGN. PERONEAL FUNCTION IMPAIRED. |

FIG. 1

| #13 | #14 | #15 | #16 |
|---|---|---|---|
| RF: ≥ (-)7° EV<br>FF: SM 1-3° VAR<br>COMPENSATION:<br>MOD TO LARGE TIB EXT ROT, MIN TO NO STJP AVAILABLE. NORMAL TO HYPOMOBILE TALAR SHIFT. 1ST RAY PF HELPS TO LOAD THE MEDIAL FF. MILD PIVOT OVER THE 5TH RAY IN PROPULSION. | RF: (-)4-6° EV<br>FF: SM 1-3° VAR<br>COMPENSATION:<br>MILD TIBIAL EXT ROT AT HEEL STRIKE, MILD TALAR SHIFT, MIDFOOT SAG & SHELFING. MILD OMJA PRONATION AT HEEL RISE. | RF: (-)1-3° EV<br>FF: SM 1-3° VAR<br>COMPENSATION:<br>FUNCTIONS BETTER THAN #16 DUE TO MILD RF UNCOMPENSATION ALLOWING IMPROVED PERONEAL FUNCTIONING. 1ST RAY CAN PF. MILD SHELFING & MOD MIDFOOT SAG. MILD TOE SIGN. | RF: 0° OR +EV<br>FF: SMALL 1-3° VARUS<br>COMPENSATION:<br>↑ed TIBIAL INT ROT vs. #12, MAX STJP AND TALAR SHIFT, POOR PERONEAL FUNCTIONING IMPAIRS 1ST RAY PF, LARGER MIDFOOT SAG (VS #12), MOD TOE SIGN. |

| #17 | #18 | #19 | #20 |
|---|---|---|---|
| RF: ≥ (-)7° EV<br>FF: MED 4-6° VAR<br>COMPENSATION:<br>AS #13, BUT LARGER 5TH RAY PIVOT & RAPID DROP OF MEDIAL FF AT TERMINAL PROPULSION. 5TH MET SHAFT BECOMES PROMINENT AND CALLUSED DUE TO EXCESSIVE LOADING. OMJA PRONATION BECOMING EXCESSIVE. | RF: (-)4-6° EV<br>FF: MED 4-6° VAR<br>COMPENSATION:<br>AS #14, BUT WITH ADDED PIVOT OVER THE 5TH MTH (MEDIAL HEEL WHIP) IN PROPULSION. MILD MIDFOOT SAG, & MOD SHELFING & TOE SIGN. OMJA PRONATION BECOMING EXCESSIVE. | RF: (-)1-3° EV<br>FF: MED 4-6° VAR<br>COMPENSATION:<br>THE FF VARUS EXCEEDS THE SMALLER RF DEFORMITY CAUSING ↑ed OMJA PRONATION. MOD MIDFOOT SAG, SHELFING & TOE SIGN. THE FOOT PIVOTS OVER THE 5TH RAY IN PROPULSION. | RF: 0° OR +EV<br>FF: MED 4-6° VAR<br>COMPENSATION:<br>↑ed TIBIAL INT ROT VS #16, MAX STJP & TALAR SHIFT, TRANSVERSE MTJ COLLAPSE (REVERSAL OF TRANSVERSE METATARSAL ARCH), SEVERE MIDFOOT SAG, & LARGE TOE SIGN. |

| #21 | #22 | #23 | #24 |
|---|---|---|---|
| RF: ≥ (-)7° EV<br>FF: LG ≥7° VAR<br>COMPENSATION:<br>↑ed HEEL WHIPPING, CAUSES SUBJECT TO KICK THEMSELVES - MAY WIDEN THEIR BASE OF SUPPORT TO AVOID THIS. ↑ed REVERSE LASTED FOOT SHAPE. | RF: (-)4-6° EV<br>FF: LG ≥7° VAR<br>COMPENSATION:<br>AS #18, BUT ↑ed PATHOLOGICAL BREAKDOWN AT THE OMJA CREATING A "REVERSE-LASTED" FOOT SHAPE. | RF: (-)1-3° EV<br>FF: LG ≥7° VAR<br>COMPENSATION:<br>AS #19, BUT EVEN GREATER 5TH RAY LOADING & PIVOT. CAUSING POSSIBLE TAILOR'S BUNION. LARGE TOE SIGN. | RF: 0° OR +EV<br>FF: LG ≥7° VAR<br>COMPENSATION:<br>AS #20, BUT MAY PIVOT OVER THE 5TH RAY IN PROPULSION. SEVERE MIDFOOT SAG & TOE SIGN. |

FIG. 2

SYSTEM AND METHOD FOR FOOT CLASSIFICATION

CROSS REFERENCES TO RELATED APPLICATIONS

This application claims the benefit of Provisional Application No. 60/665,429, filed on Mar. 24, 2005, entitled "Classification Method for Determining 24 Adult Foot Types", the entirety of which in incorporated by reference herein.

BACKGROUND OF THE INVENTION

1. Field of the Invention

This invention relates to a method of analyzing characteristics of an adult human foot. More specifically, this invention relates to a system and method for analyzing and classifying such a foot into one of twenty-four foot types.

2. Related Art

An orthosis is a device used to protect, support or improve function of parts of the body that move. A foot orthosis may be a simple, mass-produced, commercially made device that is sold over the counter in various retail stores and outlets. However, a foot orthosis may also be a custom-made device that is specifically designed to meet the needs of a particular individual.

A custom-made foot orthosis is manufactured by making an impression, also known as a "cast", of a person's foot. The impression duplicates any misalignments or deformations in the foot. Orthotic specialists can then correct the misalignments and/or deformations by employing compensation and stabilization techniques when creating the orthotic.

The finished foot orthosis is placed in an individual's shoe and helps keep the individual's foot in proper alignment. Depending upon the individual's needs, the foot orthosis may have padding to cushion the foot against the weight of the body.

In general, there are four broad categories of foot orthoses, which can be either non-custom or custom made. The four categories include:

Functional orthoses—which incorporate special wedges to adjust the heel or forefoot, correcting defects in the arch that allow for excessive motion, such as overpronation (flattening of the arch); or, that cause poor shock absorption, such as excessive supination (an arch that is too high).

Weight-dispersive or accommodative orthoses (also know as total-contact orthoses or inserts)—which typically feature padding designed to relieve pain caused by excessive pressure on the metatarsal heads or other structures of the foot. Other accommodative orthoses are designed to treat pain and pressure on the sesamoid bones, collapsed tarsal bones, sores and chronically inflamed toes.

Supportive orthoses—which are arch supports usually prescribed to treat problems of the plantar arch.

Early childhood orthoses—which are special devices designed to correct biomechanical walking problems identified in young children. They include splints, gait plates and night bars.

An individual may need a foot orthosis for a variety of reasons, including, but not limited to: correction of alignment, alleviation of pain, arch support, and the like. Failure to correct certain foot problems can lead to medical problems, including, but not limited to: plantar fasciitis, tibial tendonitis, heel spurs, and any other foot, limb or spinal condition that is mechanically induced by structural variations of the foot during gait. Accordingly, properly manufactured orthoses can prevent the need for more intrusive therapies, including surgery.

For some individuals, non-custom orthoses provide some relief. However, to achieve the best results and receive the most relief, most individuals purchase custom-made orthoses. Custom-made foot orthoses specifically address an individual's own orthotic needs. However, custom-made foot orthoses require an individual to seek professional services, i.e., schedule appointments with various doctors, therapists or other medical practitioners in the podiatric field. Additionally, it has been found that various methods utilized by health care practitioners in measuring and fitting an individual for a foot orthosis are inconsistent and lack certain components that would enhance the comfort and fit of the foot orthosis.

Despite the individualization that custom-orthoses provide, orthotic users may still experience foot, leg, and back problems. Accordingly, a method for analyzing an adult foot for a foot orthosis that would fit properly in addition to relieving pain or discomfort particular to the individual person is needed in the art. The present invention is believed to be an answer to that need.

SUMMARY OF THE INVENTION

One aspect of the present invention relates to a method of classifying a foot in a foot type. The method includes visualizing the foot; assessing a plurality of characteristics exhibited by the foot; and classifying the foot into a foot type wherein classification is based on the visualization of the foot and the assessment of the plurality of characteristics exhibited by the foot.

In another aspect, the current invention relates to a method for manufacturing a foot orthosis for a particular foot type. The method includes classifying a foot into a foot type according to the method recited above and manufacturing a foot orthosis based on the foot type. The present invention also relates to an orthosis that is manufactured by this process.

In yet another aspect, the present invention relates to a foot analysis center for analyzing a foot and classifying the foot into a foot type. The foot analysis center includes a walking platform; at least one image recording device; and a processing unit connected to the at least one image recording device and the walking platform. The processing unit facilitates a method of analyzing and classifying the foot into a foot type.

The present invention also relates to a system of classifying a foot into a foot type. The system includes twenty-four foot types, wherein each of the twenty-four foot types is based on characteristics exhibited by a foot. The system also includes evaluation means for evaluating the characteristics exhibited by the foot; comparing the characteristics exhibited by the foot to characteristics of the twenty-four classes of foot types; and classifying the foot into one of the twenty-four foot types.

These aspects, as well as others, are described in more detail below.

BRIEF DESCRIPTION OF THE FIGURES

For the purpose of illustrating the invention, the drawings show a form of the invention that is presently preferred. However it should be understood that the present invention is not limited to the precise arrangements and instrumentalities shown in the drawings, wherein:

FIG. 1 illustrates a chart of foot types 1-12.

FIG. 2 illustrates a chart of foot types 13-24.

DETAILED DESCRIPTION

The following abbreviations and acronyms are used throughout the present specification, claims and figures: RF—Rearfoot; FF—Forefoot; EV—Eversion; IV—Inversion; STJ—Subtalar Joint; STJP—Subtalar Joint Pronation; PRO—Pronation; SUP—Supination; VAR—Varus; VAL—Valgus; LG—Large; MED—Medium; MOD—Moderate; SM—Small; MIN—Minimal; MAX—Maximum/maximal; COMP—Compensated; UNCOMP—Uncompensated; GFR's—Ground Reaction Forces; ROT—Rotation; ER—External Rotation; IR—Internal Rotation; CALC—Calcaneus; RCS—Resting Calcaneal Stance; PF—Plantarflexion; DF—Dorsiflexion; TS—Talar Shift; MTJ—Midtarsal Joint; OMJA—Oblique Midtarsal Joint Axis; LMJA—Longitudinal Midtarsal Joint Axis; MFS—Midfoot Sag; TIB—Tibia; HYPO—Hypomobile; HYPER—Hypermobile; ↑—Increase; ↓—Decrease.

To overcome orthopedic and podiatric problems experienced by some individuals, utilization of a foot orthosis may be recommended. Orthoses include custom or non-custom motion control devices that can be made of rigid or semi-rigid material. Examples of orthoses include, but are not limited to: heel cups, wedges, arch supports, shoe inserts, and any other device an individual can insert into a shoe.

Determination and evaluation of certain characteristics, such as weight-bearing compensations and corresponding gait patterns of an adult's foot, can facilitate the classification of the foot into one of twenty-four foot types. Barring injury, surgical alteration or repair, or congenital deformity of the foot, individuals having the same foot type have similar gaits, callus patterns, joint laxities or immobility, predisposition to injuries and will also have similar symptoms or problems. Accordingly, an orthosis made for a particular foot type will alleviate the problems experienced by a person with that particular foot type. As discussed in more detail below, each foot type of a twenty-four foot type model demonstrates its own specific sequence of weight-bearing compensations and a corresponding gait pattern.

Figure 3:
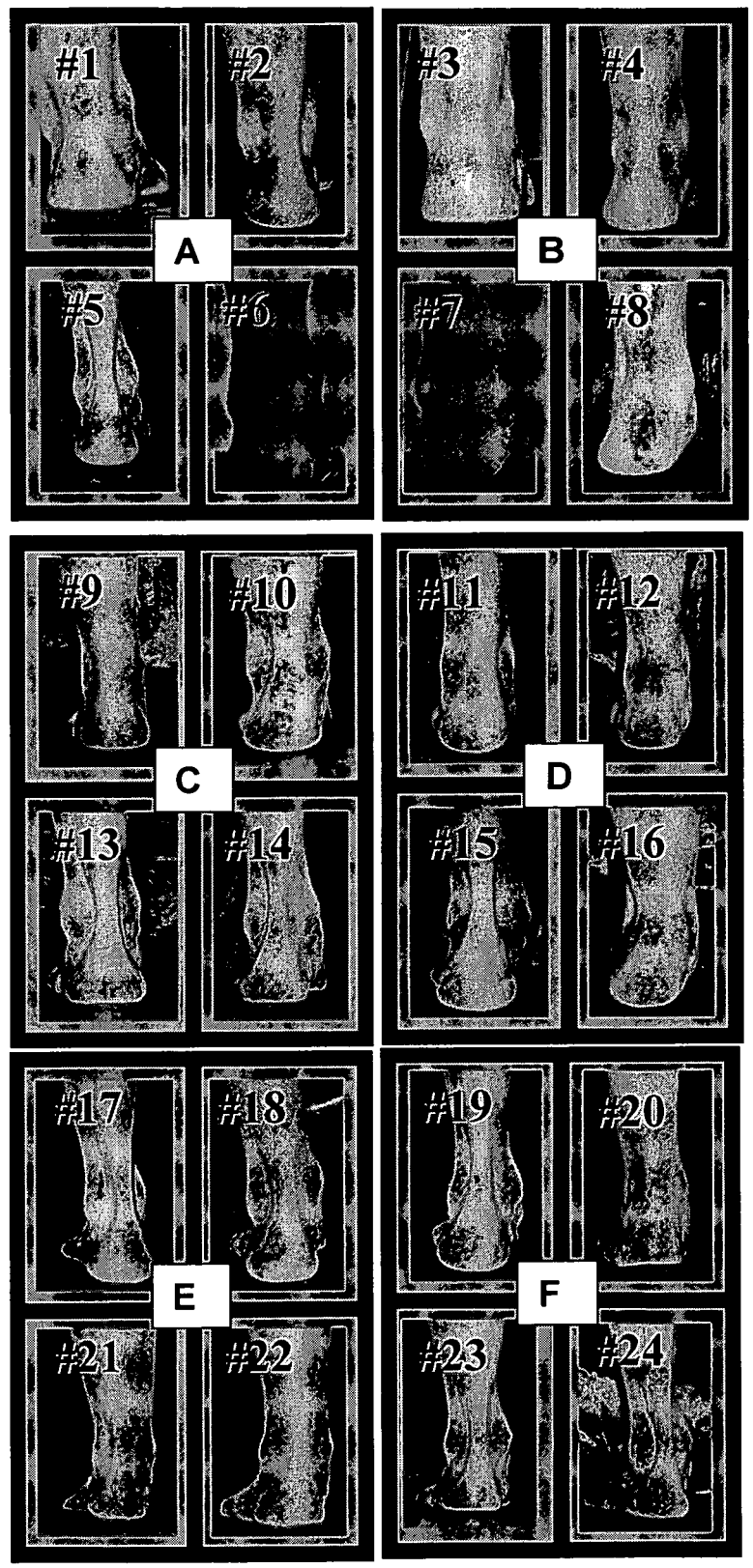
FIG. 3 illustrates photos of various foot types and subdivisions thereof.

In the present invention there are twenty-four foot types, wherein each foot type is based on characteristics exhibited by a foot. FIG. 1 illustrates the characteristics of foot types 1-12, while FIG. 2 illustrates the characteristics of foot types 13-24. Pictures of adult feet that have been classified into each of the twenty-four foot types are shown in FIG. 3.

The twenty-four foot types have been determined by analyzing rear foot and forefoot deformities of adult feet that may occur singularly, or in combinations. Individuals with the same rear foot deformities and forefoot deformities exhibit certain characteristics, and therefore examples of those characteristics are also included in the description of the twenty-four foot types.

It has been determined that there are two basic rear foot deformities that can be identified in the subtalar neutral position: varus and valgus. Rear foot valgus deformities do not commonly occur in the normal adult population and are therefore excluded from the realm of this foot typing model. Rearfoot varus deformities can then be subcategorized into four types dependent upon the amount of pronation motion that is available. Also, three basic forefoot categories can occur when an individual foot is analyzed in a non-weight bearing, prone lying position: neutral alignment, varus, or valgus.

The subtalar joint is the joint of the foot, below the ankle, where the talus and the calcaneus (heel bone) articulate. When the rear foot is in subtalar neutral, the subtalar joint is neither pronated nor supinated. When the rear foot exhibits subtalar (calcaneal) eversion, the rear foot possesses a range of motion away from the neutral position into more pronation (able to evert 5-10 degrees beyond vertical). When the rear foot exhibits subtalar (calcaneal) inversion; the rear foot possesses a range of motion away from the neutral position into more supination (able to invert 25-30 degrees from vertical). However, for the purposes of the twenty-four foot typing model, when assessing the rear foot, only the pronation measurement is taken into account since it is the measurement that enables the examiner to properly subcategorize a rear foot deformity.

The level of restricted subtalar joint pronation determines what other characteristics the individual's foot or series of compensations the individual's body will acquire after birth in order for locomotion (walking, running, etc.) to occur. Based on the subtalar joint pronation, the rear foot can exhibit a "compensated" varus or an "uncompensated" varus. A compensated rear foot varus exists when the subtalar joint can evert enough to allow the calcaneus to assume a vertical position to the ground when an individual is standing or walking. An uncompensated rear foot varus exists when the subtalar joint is restricted in eversion motion so the calcaneus remains inverted to the ground when standing or walking. This level of limitation, or uncompensation, is subcategorized as small, moderate or large.

Based on the uncompensated varus and the compensated varus rear foot deformities, there are four subcategories of rear foot deformations: (1) compensated rear foot varus; (2) small uncompensated rear foot varus; (3) moderately uncompensated rear foot varus; and (4) large uncompensated rear foot varus. These four subcategories are exemplified in FIG. 1 in foot types 12, 11, 10 and 9, respectively.

When the foot is placed in the subtalar neutral position, the forefoot can be classified as either a neutral forefoot, a forefoot varus deformity or a forefoot valgus deformity. Forefoot alignment is typically assessed by using a goniometer, while the individual is in the subtalar neutral position, by measuring the angular relationship of the plane of the forefoot (the ball of the foot), to the bisection of the posterior aspect of the calcaneus.

When the plane of the forefoot is at a right angle to the posterior bisection of the calcaneus, the forefoot is classified as neutral. Foot types 9, 10, 11 and 12 are illustrative of foot types having a neutral forefoot. Photographs of foot types 9, 10, 11 and 12 are shown in FIG. 3.

When the plane of the forefoot is angled in an inverted (or supinated) position relative to the posterior bisection of the calcaneus, the forefoot is classified as having a forefoot varus deformity. The level of this deformity can be classified into three subcategories based on the severity of the deformity: (1) small varus deformities, which measure 1-3° varus angle; (2) moderate varus deformities, which measure 4-6° varus angle; and (3) large varus deformities, which measure $\geq 7°$ varus angle. These three subcategories are exemplified by foot types 16, 20 and 24, respectively, as shown in FIG. 2 and photographically illustrated in FIG. 3.

When the plane of the forefoot is angled in an everted (or pronated) position relative to the posterior bisection of the calcaneus, the forefoot is classified as having a forefoot valgus deformity. This forefoot deformity is less common than the forefoot varus deformity, and can be classified into two subcategories based on the severity of the deformity: (1) small valgus deformities, which are measured to be at 1-6° valgus angle and are usually found to be flexible; and (2) large valgus deformities, which are measured to be $\geq 7°$ valgus angle and are usually found to be rigid. These two subcategories are exemplified by foot types 8 and 4, respectively, as shown in FIG. 1 and illustrated photographically in FIG. 3.

Within the twenty-four foot types, foot types 4, 8, 16, 20 and 24 have a primary foot deformity in the forefoot and according to traditional podiatric theory, these foot types do not exhibit any rear foot deformity since traditional podiatric belief is that the small compensated rear foot varus deformity is a "normal rear foot". However, in this foot typing classification method the compensated rear foot varus, although small, is considered to be one of the four rear foot deformities noted previously.

Foot types 9-12 have a primary foot deformity in the rear foot, i.e., there are no forefoot deformities. However, fifteen foot types have combined deformities, i.e., the foot type exhibits both a rear foot deformity and a forefoot deformity. As shown in Tables 1 and 2 below, foot types 1-3, 5-7, 13-15, 17-19 and 21-23 have combined rear and forefoot deformities.

TABLE 1

Rearfoot Varus With Forefoot Valgus Foot Types

| Foot Type | Rear Foot Deformity | Forefoot Deformity |
|---|---|---|
| 1 | Large Uncompensated Rearfoot Varus | Large Rigid Forefoot Valgus |
| 2 | Moderately Uncompensated Rearfoot Varus | Large Rigid Forefoot Valgus |
| 3 | Small Uncompensated Rearfoot Varus | Large Rigid Forefoot Valgus |
| 5 | Large Uncompensated Rearfoot Varus | Small Flexible Forefoot Valgus |
| 6 | Moderately Uncompensated Rearfoot Varus | Small Flexible Forefoot Valgus |
| 7 | Small Uncompensated Rearfoot Varus | Small Flexible Forefoot Valgus |

TABLE 2

Rearfoot Varus With Forefoot Varus Foot Types

| Foot Type | Rear Foot Deformity | Forefoot Deformity |
|---|---|---|
| 13 | Large Uncompensated Rearfoot Varus | Small Forefoot Varus |
| 14 | Moderately Uncompensated Rearfoot Varus | Small Forefoot Varus |
| 15 | Small Uncompensated Rearfoot Varus | Small Forefoot Varus |
| 17 | Large Uncompensated Rearfoot Varus | Medium Forefoot Varus |
| 18 | Moderately Uncompensated Rearfoot Varus | Medium Forefoot Varus |
| 19 | Small Uncompensated Rearfoot Varus | Medium Forefoot Varus |
| 21 | Large Uncompensated Rearfoot Varus | Large Forefoot Varus |
| 22 | Moderately Uncompensated Rearfoot Varus | Large Forefoot Varus |
| 23 | Small Uncompensated Rearfoot Varus | Large Forefoot Varus |

In addition to the various rear foot and forefoot deformities displayed in the different foot types, each of the twenty-four foot types also has characteristics unique to each particular foot type. As shown in FIGS. 1 and 2, the foot types often have certain compensation characteristics associated with them. By evaluating and comparing the characteristics exhibited by an individual's foot to the characteristics shown in the twenty-four foot types, that individual's foot can then be classified into one of the twenty-four foot types.

To evaluate and classify an individual's foot into one of the above-described twenty-four foot types, a medical practitioner can utilize a goniometer, which is an instrument for measuring angles, to calculate rear foot and forefoot deformities exhibited by the individual. While utilization of a goniometer to measure an individual for orthoses is widely practiced, it is often unreliable as different practitioners may take measurements differently, which would result in an incorrect classification of the foot.

Alternatively, to evaluate and classify a foot into one of the twenty-four foot types, the medical practitioner can visualize, observe or otherwise inspect the shape of the individual's foot and calluses, in addition to studying that individual's foot as the individual stands still in addition to visualizing that individual's characteristic gait as they ambulate on a walking platform such as a level floor, a mat, a treadmill or other similar level surface. By having the medical practitioner observe specific characteristics exhibited by the foot while the foot is in a standing position or while the individual is walking or running, the medical practitioner can compare those characteristics to the defined characteristics of the twenty-four foot types.

Typically, the medical practitioner will take still pictures and/or video of the individual's feet while the individual is standing still or is walking or jogging on a walking platform. The pictures or video can be taken from any view point, but typically the pictures or video is taken from a posterior (rear) view. After observing the individual's foot in a standing position and/or during a walking or jogging motion and taking some measurements of the individual's foot and leg, the practitioner can then make certain assessments that will lead to classification into one of twenty-four foot types.

When analyzing or evaluating an adult foot and classifying the adult foot into one foot type, several steps are employed. In general, the medical practitioner visualizes the foot both in while the foot is in a standing position and during gait. The characteristics of the foot, such as the foot shape and the foot structures, along with other characteristics of the lower limb, are studied in order to interpret the various forefoot and rear foot deformities that may exist. Visualization can be done either while the individual is standing still, or while the individual is walking or jogging on walking platform. Alternatively, visualization can be done by watching a video or looking at still photos of the individual walking or running on the walking platform.

Visualization of the individual's foot can take place in a medical practitioner's office, a laboratory, a retail outlet, or any other location that can provide a place for the individual to walk or jog while a medical practitioner observes the foot. Alternatively, an individual may make, or have another individual assist them in making a video or taking still photos of their foot in a standing position or during a walking or jogging motion. The video and/or still photos can be sent to a medical practitioner's office or orthosis manufacturer, which can classify the foot and produce an orthosis based on that individual's foot type.

When visualizing the individual's foot, the practitioner assesses calcaneal alignment with the floor, talar stability within the talocrural joint, tibial and femoral limb rotations, triplanar midtarsal joint compensatory mechanisms, and first and fifth ray compensatory mechanisms, which includes midfoot sag (which is a vertical drop in arch height), and midfoot shelfing (which is a horizontal shifting of the arch towards the midline of the body without any associated drop in arch height).

Other characteristics of the foot are also observed or visualized. Such characteristics include, but are not limited to:

arch height, calcaneal bumps or exostoses, infracalcaneal fat pad migration, calluses, and the like. The observed characteristics of the individual's foot are compared to the characteristics of the twenty-four foot types as outlined in FIGS. 1 and 2.

Figure 4:
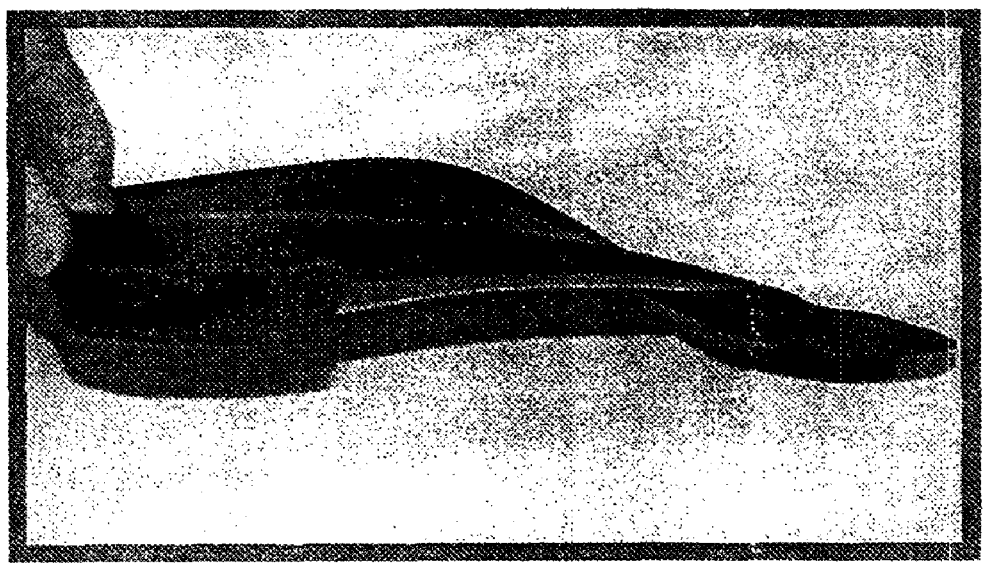
FIG. 4 illustrates an example of an orthosis.

After the individual's foot has been analyzed and has been classified into a single foot type, an orthosis can be made based on the assigned foot type. FIG. 4 illustrates an orthosis designed and configured in accordance with the present invention. Thus, this foot typing model suggests that each individual foot type has its own specific orthosis design and corrections, based on the particulars of that foot's functioning in gait. The orthosis may either be custom-made based on an impression of the individual's foot or non-custom made and solely based on the individual's foot type. It is noted that an individual may have a different foot type for each foot.

To make a custom-made orthosis based on the individual's foot type, a cast or impression of the individual's foot is made. Methods of producing casts are generally known to those with ordinary skill in the art.

An orthosis can then be manufactured based on the impression of the individual's foot. The orthosis is manufactured by any process known in the art, and can be made out of a variety of rigid or semi-rigid materials such as carbon fiber, polypropylene, copolymers, and open and closed cell foams. Knowledge of this foot typing method adds specificity to custom orthosis manufacturing parameters for each foot type, and eliminates gross errors or failed treatments that commonly occur in the industry today due to lack of such specificity.

Non-custom orthoses can also be made for each of the twenty-four foot types. The non-custom orthoses are made based on the characteristics of each foot type. The twenty-four non-custom made orthoses may be mass-produced and sold through retail stores, specialty stores or through medical personnel offices, such as doctors' offices, therapists' offices, hospitals, and the like.

Further, it is contemplated that shoe soles can be manufactured based on the twenty-four foot types. Manufacture of shoe soles that specifically address an individual's foot type would allow the individual to purchase shoes that would correct various symptoms, and alleviate any discomfort or pain experienced by the individual. Processes of manufacturing shoe soles are known in the art. Such processes would be adapted to produce shoe soles that complement each of the twenty-four foot types.

It is contemplated that one shoe sole can be made for each one of the twenty-four foot types, i.e., twenty-four shoe soles would be manufactured, one for each foot type. However, it is also contemplated that subdivisions of the twenty-four foot types can be created to simplify the marketing and production of the shoe soles, and likewise the production and marketing of orthoses.

Division of the twenty-four foot types into subdivisions is based on foot types that are adjacent to one another in FIG. 3. The feet adjacent to one another function relatively similarly, and thus have similar correctional needs. Thus, it would be possible to design a shoe sole that could provide adequate support and control for more than one foot type. Some examples of subdivisions of the twenty-four foot types include groups of four foot types ("quads") that are adjacent to each other if FIG. 3. According to FIG. 3., the subdivisions are divided into are six quads, wherein each quad has four foot types. Quad A includes foot types 1, 2, 5 and 6. Quad B includes foot types 3, 4, 7 and 8. Quad C includes foot types 9, 10, 13 and 14. Quad D includes foot types 11, 12, 15 and 16. Quad E includes foot types 17, 18, 21 and 22. Finally, Quad F includes foot types 19, 20, 23 and 24. The four foot types in each quad function somewhat similarly to one another, and accordingly, a shoe sole can be made based on that quad to correct deformities and alleviate pain and discomfort.

It is contemplated that a medical practitioner can analyze and classify a foot into one foot type in an all-inclusive center available in his or her office, which may be equipped with walking platform, and at least one image recording device such as a digital camera or video recorder. The center may also include a processing unit, such as a desk top or lap top computer, which can be connected to the Internet for orthosis ordering and technical support purposes. The processing unit would typically be connected to the walking platform, and at least one image recording device.

The processing unit of the analyzing and classifying center would facilitate the determination of the foot type for the particular adult utilizing the treadmill or other walking platform. The processing unit may be equipped with software or functions that allow a practitioner to view the recorded video or pictures and manipulate this data to classify the foot into at least one adult foot type.

The center can also include consumer information which would provide educational information about each foot type and orthosis and shoe needs for that foot type.

One or more embodiments of the present invention have been described. Nevertheless, it will be understood that various modifications may be made without departing from the spirit and scope of the invention. Accordingly, other embodiments are within the scope of the following claims.

I claim:

1. A method of classifying a foot into a foot type, the method comprising:
   visualizing a foot of an individual;
   assessing characteristics exhibited by said foot with a goniometer, said characteristics comprise: rearfoot position; forefoot position; calcaneal alignment to a floor; talar stability; tibial and femoral limb rotation; and triplanar midtarsal joint compensatory mechanisms; and
   classifying said foot into a foot type selected from a group of twenty-four foot types, each of said twenty-four foot types based on two or more of said characteristics exhibited by a plurality of feet,
   said classifying being based on said visualizing of said foot, said assessing of said characteristics exhibited by said foot and comparing said characteristics exhibited by said foot to said two or more characteristics of said twenty-four foot types.

2. A method according to claim 1, wherein when said foot is visualized, said foot is in a standing position.

3. A method according to claim 1, wherein when said foot is visualized, said foot is in a walking or running motion.

4. A method according to claim 1, wherein when said foot is visualized, said foot is visualized while in a standing position and while in a walking or running motion.

5. A method according to claim 1, wherein when said characteristics of said foot further comprise: first and fifth ray compensatory mechanisms; assessing arch height of said foot; and assessing said foot for calluses and calcaneal bumps.

6. A method according to claim 1, wherein said foot type is selected from a plurality of subdivisions within said twenty-four foot types.

7. A method for manufacturing a foot orthosis for a particular foot type, the method comprising the steps of: classifying a foot into a foot type as recited in claim 1; and manufacturing a foot orthosis based on said foot type.

8. A method according to claim 7, wherein said foot orthosis is selected from group consisting of a non-custom orthosis and a custom orthosis.

9. A foot orthosis manufactured by a method as recited in claim 7.

10. A method for manufacturing a shoe sole for a particular foot type, the method comprising the steps of:
classifying a foot into a foot type as recited in claim 1; and
manufacturing a shoe sole based on said foot type.

11. A shoe sole manufactured by a method as recited in claim 10.

12. A method according to claim 1, wherein when said characteristics of said foot further comprise midfoot sag and midfoot shelfing.

13. A method according to claim 1, wherein each foot type of said twenty-four foot types demonstrates a specific sequence of weight bearing compensations and a corresponding gait pattern.

14. A method according to claim 1, wherein when said foot is visualized, said foot is in a walking motion or a running motion to assess said foot's functioning in gait.

15. A method according to claim 1, wherein when said foot is visualized, said foot's shape and structures along with characteristics of a lower limb of said individual are studied.

16. A method according to claim 1, wherein when said foot is visualized, said visualizing is done by at least one of watching a video and looking at still photographs of said individual standing still and in a walking motion or a running motion.

17. A method according to claim 1, wherein said classifying step is performed with the aid of a processing unit.

18. A method according to claim 4, wherein when said foot is classified, said characteristics of said foot in each of said standing position and said walking or running motion are compared to said two or more characteristics of said twenty-four foot types.

* * * * *